United States Patent [19]

Cotter et al.

[11] Patent Number: 4,500,471

[45] Date of Patent: Feb. 19, 1985

[54] PREPARATION OF TRIFLUOROMETHYL-BENZOYL HALIDES

[75] Inventors: Byron R. Cotter, Grand Island; David Y. Tang, Amherst, both of N.Y.

[73] Assignee: Occidental Chemical Corporation, Niagara Falls, N.Y.

[21] Appl. No.: 140,894

[22] Filed: Apr. 16, 1980

[51] Int. Cl.$^3$ .............................................. C07C 63/10
[52] U.S. Cl. ......................... 260/544 D; 260/465 D; 260/543 R
[58] Field of Search ........... 260/544 D, 544 F, 543 R, 260/465 D

[56] References Cited

U.S. PATENT DOCUMENTS

| | | | |
|---|---|---|---|
| 2,181,554 | 11/1939 | Kracker et al. | 260/544 F |
| 3,935,258 | 1/1976 | Hempel et al. | 71/120 |
| 4,079,089 | 3/1978 | Klauke . | |
| 4,079,090 | 3/1978 | Buttner et al. . | |
| 4,093,669 | 6/1978 | Klauke . | |

OTHER PUBLICATIONS

Lichtenberger, Jean et al., *Bull. Soc. Chim.*, (1962), pp. 915–919, of Memoires.

Advances in Fluorine Chemistry, (1970), vol. 6, p. 2, Butterworths London Publ.

Strogyn, Eugene L., *J. of Medicinal Chemistry*, (1973), pp. 1399–1401.

*Primary Examiner*—Natalie Trousof
*Assistant Examiner*—L. Hendriksen
*Attorney, Agent, or Firm*—J. F. Tao; A. S. Cookfair

[57] ABSTRACT

Trifluoromethylbenzoyl chlorides are prepared by the reaction of trichloromethylbenzoyl chlorides or tribromomethylbenzoyl bromides with about 3 moles or less of hydrogen fluoride in the presence of a halogen transfer catalyst.

17 Claims, No Drawings

PREPARATION OF TRIFLUOROMETHYL-BENZOYL HALIDES

BACKGROUND OF THE INVENTION

This invention relates to a process for the preparation of trifluoromethylbenzoyl chlorides, and bromides. The products are useful intermediates in the production of various dyestuffs and agricultural chemical products.

It is known to prepare trifluoromethylbenzoyl chloride by reaction of trifluoromethylbenzoic acid with thionyl chloride. The starting material for such reaction, trifluoromethylbenzoic acid may be prepared by several methods, each of which is a multistepped process involving relatively expensive starting materials and/or intermediates. Thus, for example, it is known to prepare trifluoromethylbenzoic acid by cyanation of bromo-benzotrifluoride, and hydrolysis of the resulting cyano-benzotrifluoride. In another known method, bromo-benzotrifluoride is reacted with magnesium and the resultant Grignard reagent is reacted with carbon dioxide to form trifluoromethylbenzoic acid. In still another method, xylene may be oxidized to toluic acid, esterified and the methyl group chlorinated and then fluorinated to yield trifluoromethylbenzoic acid.

Although the processes of the prior art are useful for the preparation of trifluoromethylbenzoyl chloride, it will be appreciated that improvements in the efficiency, economy of preparation and yield of the desired product are nevertheless desirable.

Accordingly, it is an object of this invention to provide an improved process for the preparation of trifluoromethylbenzoyl halides. It is a more specific object to provide a simple, direct process for the preparation of trifluoromethylbenzoyl chloride, based on the use of readily available, economical starting materials and reactants.

SUMMARY OF THE INVENTION

In accordance with the present invention it has been found that trifluoromethylbenzoyl halides of the formula

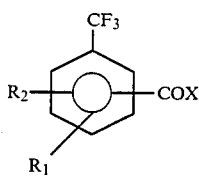

wherein X is chlorine or bromine and $R_1$ and $R_2$ are independently selected from the group consisting of hydrogen, fluorine, chlorine, bromine, alkyl, aryl, haloaryl, alkoxy, fluoroalkoxy, aryloxy, haloaryloxy, nitro, cyano, sulfonyl, and carboxylic acid chloride, may be prepared by the reaction of benzoyl chlorides or bromides of the formula

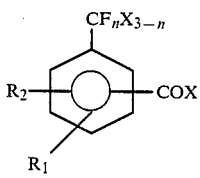

wherein X, $R_1$ and $R_2$ are as stated above, and n is 0 to 2 with about 3-n moles or less of hydrogen fluoride in the presence of a halogen transfer catalyst.

The preferred alkyl, alkoxy and fluoroalkoxy groups represented by $R_1$ and $R_2$ are those of one to six carbon atoms, and most preferably methyl, methoxy, and fluoromethoxy groups. The preferred aryl and aryloxy groups are phenyl and phenoxy or substituted phenyl and phenoxy groups wherein substituents such as chloro-, fluoro-, bromo-, nitro-, cyano-, methyl-, or carboxylic acid chloride are present on the ring. In addition to the $R_1$ and $R_2$ substituents identified hereinabove, various other ring substituents which are stable and inert under the reaction conditions of the process of the invention, may be present. Thus, in accordance with the process of this invention, substituted or unsubstituted trichloromethylbenzoyl chlorides, dichlorofluoromethylbenzoyl chlorides, chlorodifluoromethylbenzoyl chlorides, tribromomethylbenzoyl bromides, dibromofluoromethylbenzoyl bromides, and bromodifluoromethylbenzoyl bromides may be reacted with hydrogen fluoride in the presence of a halogen transfer catalyst to produce the corresponding substituted or unsubstituted trifluoromethylbenzoyl chloride or bromide.

In the halogen exchange process of the invention, the hydrogen fluoride is reacted with the trihalomethylbenzoyl chloride or bromide in an amount sufficient to replace the chlorine or bromine atoms of the trihalomethyl group with fluorine. Thus, for example, one mole of trichloromethylbenzoyl chloride may be reacted with three moles of hydrogen fluoride in the presence of a halogen transfer catalyst, to selectively fluorinate the methyl group. It is surprising that trifluoromethylbenzoyl chlorides or bromides are formed selectively and in high yield by the process of the invention, rather than a mixed product containing a statistical distribution of the fluorine atoms on the trihalomethyl group and the acid halide group. In addition to the fluorination that occurs as a result of reaction with the hydrogen fluoride, a halogen exchange occurs during the reaction, in the presence of the halogen transfer catalyst, that results in the selective distribution and/or re-distribution of the fluorine atoms. Such selective halogen exchange is disclosed in co-pending application Ser. No. 140,893 filed Apr. 16, 1984, now abandoned, the disclosure of which is incorporated by reference herein.

DESCRIPTION OF PREFERRED EMBODIMENTS

The preferred starting materials for the process of this invention are trichloromethylbenzoyl chlorides characterized by the formula

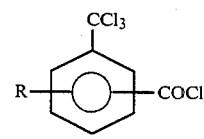

wherein R is hydrogen, chloro-, fluoro-, bromo-, nitro-, cyano- or methyl-; and most preferably, the compounds m-trichloromethylbenzoyl chloride and p-trichloromethylbenzoyl chloride. These compounds are reacted with three moles or less of hydrogen fluoride, in the presence of a halogen transfer catalyst, to prepare the corresponding trifluoromethylbenzoyl chlorides.

The fluorination reaction in accordance with the invention, is carried out in the presence of a halogen transfer catalyst. Such catalysts are well known in literature and include for example ferric chloride, aluminum chloride, molybdenum pentachloride, titanium tetrachloride, antimony pentafluoride, antimony pentachloride, antimony-V-chloride-fluoride, and the like. The preferred catalyst is antimony pentachloride. Typically, the catalyst is employed in amounts of about 0.01 to about 10 percent by weight and preferably about 0.1 to about 3 percent by weight based on the weight of trichloromethylbenzoyl chloride starting material.

The process of the invention may be carried out over a wide range of conditions. The process is preferably carried out at atmospheric pressure, however subatmospheric and superatmospheric pressures may be employed if desired. The temperature range under atmospheric conditions may vary between the melting point and the boiling point of the reaction mixture. Preferably however the reaction is carried out in a temperature range from about 0° to about 100° Celsius and most preferably from about 50° to about 80° Celsius.

Although it is preferred to carry out the reaction neat, a suitable inert solvent may be employed if desired. Suitable solvents include for example, nitro benzene, carbon disulfide, and the like.

The desired product, trifluoromethylbenzoyl chloride, is conveniently removed from the reaction product by conventional means such as fractional distillation. Under-fluorinated reaction products such as chloro-difluoromethyl-benzoyl chloride, dichlorofluoromethylbenzoyl chloride, and the like may be recycled for further reaction in accordance with the invention. Over fluorinated products such as trifluoromethylbenzoyl fluoride may be converted to trifluoromethylbenzoyl chloride by halogen exchange reaction in admixture with trichloromethylbenzoyl chloride in the presence of a halogen transfer catalyst in accordance with the process of copending application Ser. No. 140,893, now abandoned.

It is a particular advantage of this invention that the desired product, such as trifluoromethylbenzoyl chloride, may be economically prepared from readily available, inexpensive starting materials in a simple, direct manner, requiring relatively few process steps. Thus, for example, xylene may be chlorinated in a known manner to prepare bis(trichloromethyl)benzene, which then may be readily hydrolyzed, for example by reaction with one mole of water, preferably in the presence of a catalyst, such as ferric chloride, to yield trichloromethylbenzoyl chloride. The trichloromethylbenzoyl chloride may then be selectively fluorinated by reaction with about three moles of hydrogen fluoride in the presence of a halogen transfer catalyst to yield trifluoromethylbenzoyl chloride. Thus, in a simple direct method, requiring only three process steps, trifluoromethylbenzoyl chloride may be synthesized from a readily available commodity chemical, such as xylene. In addition, various other substituted xylenes, bearing ring substituents stable to the process steps may be employed as starting materials to produce correspondingly substituted trifluoromethylbenzoyl chlorides. Furthermore, it will be apparent that various other methylbenzene starting materials, such as mesitylene or durene, may be employed in a similar fashion to produce trifluoromethylbenzoyl chlorides having more than one trifluoromethyl and/or acyl chloride group present.

In a particular embodiment, the present invention provides a process for the preparation of trifluoromethylbenzoyl chloride comprising the steps of (A) hydrolyzing bis(trichloromethyl)benzene by reaction with about one mole of water to form trichloromethylbenzoyl chloride, and (B) reacting the trichloromethylbenzoyl chloride with about three moles or less of hydrogen fluoride, in the presence of a halogen transfer catalyst, to yield trifluoromethylbenzoyl chloride.

The following specific examples are provided to further illustrate the invention in a manner in which they be carried out. It will be understood, however, that the specific details given in the examples have been chosen for purposes of illustration and are not to be construed as a limitation on the invention. In the examples, unless otherwise indicated, all parts and percentages are by weight and all temperatures are in degrees Celsius.

EXAMPLE 1

(A) A mixture of 626 parts of 1,4-bis(trichloromethyl)benzene and 3.1 parts of ferric chloride was charge to a reaction vessel equipped with a condenser. The mixture was heated and maintained at about 120°–130° C. while 34.2 parts of water was added, over a period of about 5 hours. The reaction product consisted of about 10% terephthaloyl chloride, about 74.2% 4-trichloromethylbenzoyl chloride and about 15.4% of 1,4-bis(trichloromethyl)benzene. The product was then fractionally distilled to recover essentially pure 4-trichloromethylbenzoyl chloride.

(B) A mixture of 25.8 parts of the 4-trichloromethylbenzoyl chloride prepared as in Example 1A, above, and 0.26 parts of antimony pentachloride was charged to a reactor and heated to about 70°–75° C. The liquid mixture was maintained at about 70°–75° C., with stirring, while HF vapor was bubbled into the bottom of the reactor over a period of about 45 minutes until a total of about 2.2 parts of anhydrous HF has been added. The mixture was maintained at temperature, with stirring, for an additional 30 minutes, then cooled to about room temperature. The reaction product, based on gas chromatographic analysis was found to contain approximately 38% 4-trifluoromethylbenzoyl fluoride; 56% 4-trifluoromethylbenzoyl chloride; about 5% of mixed 4-fluorochloro-methylbenzoyl halides and less than 1.0% 4-trichloromethylbenzoyl chloride. The structure of the major product component, 4-trifluoromethylbenzoyl chloride was confirmed by spectral analyses.

EXAMPLE 2

A mixture of about 103 parts of 4-trichloromethylbenzoyl chloride and 1.0 parts of antimony pentachloride was charged to a reactor and heated to 65°–70° C. The mixture was maintained at about that temperature with stirring over a 90 minute period while 16 parts of HF vapor was bubbled into the bottom of the reactor. The mixture was maintained at temperature, with stirring, for an additional hour, then cooled to about room temperature. The product analyzed by gas chromatographic techniques was found to contain about 35% 4-trifluoromethylbenzoyl fluoride; 55% 4-fluoromethylbenzoyl chloride; less than 10% of mixed 4-fluorochloro-methylbenzoyl halides and less than 1% 4-trichloromethylbenzoyl chloride.

EXAMPLE 3

A quantity of 3-trichloromethylbenzoyl chloride was prepared by hydrolysis of 1,3-bis-(trichloromethyl)benzene with one mole of water in the presence of a catalytic amount of FeCl₃. A mixture of 9.2 parts of the 3-trichloromethylbenzoyl chloride and 0.1 parts of antimony pentachloride was charged to a reactor and heated to about 60° C. The liquid mixture was maintained at about 60° C., with stirring, while HF vapor was bubbled into the bottom of the reactor until a total of about 2.2 parts of anhydrous HF had been added. The mixture was maintained at temperature, with stirring, for an additional hour, then cooled to about room temperature. The product was analyzed by gas chromatographic techniques as well as by spectral analyses. The major product was found to be 3-trifluoromethylbenzoyl chloride. The distribution of components in the reaction product as determined by gas chromatographic techniques, was approximately 18.4% 3-trifluoromethylbenzoyl fluoride; 52.0% 3-trifluoromethylbenzoyl chloride; less than 1% mixed 3-fluoro-chloromethyl benzoyl halides; and about 21% 3-trichloromethyl benzoyl chloride.

When the general process of Examples 1B, 2, or 3 is repeated except that tribromomethylbenzoyl bromide is employed in substitution for the trichloromethylbenzoyl chloride starting material, a product containing trifluoromethylbenzoyl bromide as the major reaction product is obtained. Similarly, when various substituted trichloromethylbenzoyl chlorides or tribromomethylbenzoyl chlorides, having nuclear substituents R₁ and/or R₂ as defined hereinabove, are employed as the starting materials, the equivalent substituted trifluoromethylbenzoyl chlorides or trifluoromethylbenzoyl bromides are obtained.

What is claimed is:

1. A process for the preparation of trifluoromethylbenzoyl halides of the formula

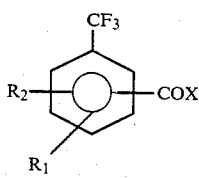

wherein X is chlorine or bromine and R₁ and R₂ are independently selected from the group consisting of hydrogen, fluorine, chlorine, bromine, alkyl, aryl, haloaryl, alkoxy, fluoroalkoxy, aryloxy, haloaryloxy, nitro, cyano, sulfonyl, and carboxylic acid chloride, which comprises reacting a compound of the formula

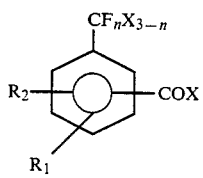

wherein X, R₁ and R₂ are as stated above, and n is 0 to 2 with about three moles or less of hydrogen fluoride in the presence of a halogen transfer catalyst.

2. A process for the preparation of trifluoromethylbenzoyl halides of the formula

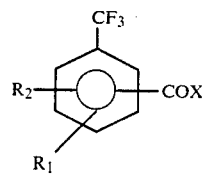

wherein X is chlorine or bromine and R₁ and R₂ are independently selected from the group consisting of hydrogen, fluorine, chlorine, bromine, alkyl, aryl, haloaryl, alkoxy, fluoroalkoxy, aryloxy, haloaryloxy, nitro, cyano, sulfonyl, and carboxylic acid chloride, which comprises reacting a compound of the formula

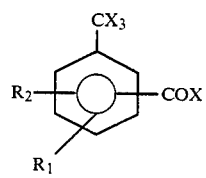

wherein X, R₁, and R₂ are as stated above, with about three moles or less of hydrogen fluoride in the presence of a halogen transfer catalyst.

3. A process according to claim 2 wherein trifluoromethylbenzoyl chloride is prepared by reacting trichloromethylbenzoyl chloride with about three moles or less of hydrogen fluoride in the presence of a halogen transfer catalyst.

4. A process according to claim 3 wherein said trifluoromethylbenzoyl chloride is 3-trifluoromethylbenzoyl chloride and said trichloromethylbenzoyl chloride is 3-trichloromethylbenzoyl chloride.

5. A process according to claim 3 wherein said trifluoromethylbenzoyl chloride is 4-trifluoromethylbenzoyl chloride and said trichloromethylbenzoyl chloride is 4-trichloromethylbenzoyl chloride.

6. A process according to claim 2, carried out at atmospheric pressure.

7. A process according to claim 6, carried out at a temperature of between about 0° and about 100° Celsius.

8. A process according to claim 7 wherein the halogen transfer catalyst is antimony pentachloride.

9. A process for the preparation of 3-trifluoromethylbenzoyl chloride which comprises reacting 3-trichloromethylbenzoyl chloride with about three moles or less of hydrogen fluoride at a temperature of between about 0° and 100° Celsius in the presence of a halogen transfer catalyst.

10. A process according to claim 9 wherein the halogen transfer catalyst is antimony pentachloride.

11. A process for the preparation of 4-trifluoromethylbenzoyl chloride which comprises reacting 4-trichloromethylbenzoyl chloride with about three moles or less of hydrogen fluoride at a temperature of between about 0° and about 100° Celsius in the presence of a halogen transfer catalyst.

12. A process according to claim 11 wherein the halogen transfer catalyst is antimony pentachloride.

13. A process for the preparation of trifluoromethylbenzoyl chlorides which comprises the steps of
   (A) hydrolyzing bis(trichloromethyl)benzene with about one mole of water to form trichloromethylbenzoyl chloride, and (B) reacting the trichloromethylbenzoyl chloride with about three moles or less of hydrogen fluoride, in the presence of a halogen transfer catalyst.

14. A process according to claim 13 wherein the bis(trichloromethyl)benzene is 1,3-bis(trichloromethyl)benzene.

15. A process according to claim 14 wherein the halogen transfer catalyst is antimony pentachloride.

16. A process according to claim 13 wherein the bis(trichloromethyl)benzene is 1,4-bis(trichloromethyl)benzene.

17. A process according to claim 16 wherein the halogen transfer catalyst is antimony pentachloride.

* * * * *